United States Patent
Amin et al.

(10) Patent No.: US 11,547,493 B2
(45) Date of Patent: Jan. 10, 2023

(54) CONNECTOR TO COUPLE SURGICAL INSTRUMENT WITH NAVIGATION SYSTEM

(71) Applicant: Acclarent, Inc., Irvine, CA (US)

(72) Inventors: Behnam Amin, Mission Viejo, CA (US); Masood H. Siddiqui, Irvine, CA (US); Itzhak Fang, Irvine, CA (US); William J. Kane, Newport Coast, CA (US)

(73) Assignee: Acclarent, Inc., Irvine, CA (US)

( * ) Notice: Subject to any disclaimer, the term of this patent is extended or adjusted under 35 U.S.C. 154(b) by 399 days.

(21) Appl. No.: 16/712,254

(22) Filed: Dec. 12, 2019

(65) Prior Publication Data

US 2020/0188035 A1    Jun. 18, 2020

Related U.S. Application Data

(60) Provisional application No. 62/780,384, filed on Dec. 17, 2018.

(51) Int. Cl.
*A61B 34/20*    (2016.01)
*A61B 17/00*    (2006.01)
(Continued)

(52) U.S. Cl.
CPC .............. *A61B 34/20* (2016.02); *A61B 17/24* (2013.01); *A61B 2017/0042* (2013.01);
(Continued)

(58) Field of Classification Search
CPC .................... A61B 17/24; A61B 34/20; A61B 2017/00199; A61B 2017/0042;
(Continued)

(56) References Cited

U.S. PATENT DOCUMENTS 3,252,124 A * 5/1966 Hansen ................. H01R 24/84
439/294
4,703,989 A * 11/1987 Price ..................... H01R 24/62
439/283
(Continued)

OTHER PUBLICATIONS

U.S. Appl. No. 62/658,688, entitled "Curette with Navigation Sensor," filed Mar. 17, 2018.
(Continued)

*Primary Examiner* — Jocelin C Tanner
(74) *Attorney, Agent, or Firm* — Frost Brown Todd LLC

(57) ABSTRACT

A surgical instrument assembly includes a surgical instrument having an instrument body, an elongate member with a distal end configured to be inserted into an anatomical passageway of a patient, a sensor operable to generate a signal corresponding to a location of the elongate member, and a first electrical connector electrically coupled with the sensor. The assembly further includes a cable assembly having a cable that communicates with a processor, and a coupling that releasably couples with the instrument body. The coupling includes a coupling body having first and second lateral sides that extend parallel to one another and are configured to extend parallel to a side of the instrument body when the coupling is coupled with the instrument body. The coupling includes a second electrical connector that electrically couples with the first electrical connector to transmit the signal from the sensor proximally through the cable and toward the processor.

20 Claims, 11 Drawing Sheets

(51) Int. Cl.
*A61B 17/24* (2006.01)
*A61B 90/00* (2016.01)
(52) U.S. Cl.
CPC .............. *A61B 2017/00199* (2013.01); *A61B 2017/00477* (2013.01); *A61B 2034/2051* (2016.02); *A61B 2090/3762* (2016.02); *A61B 2217/005* (2013.01)
(58) Field of Classification Search
CPC A61B 2017/00433; A61B 2017/00455; A61B 2017/00477; A61B 2017/00411; A61B 2017/00464; A61B 2034/2072; A61B 2034/2051; A61B 2090/3762; A61B 2090/3612; A61B 2217/005; A61M 1/84; H01R 13/5224
See application file for complete search history.

(56) References Cited

U.S. PATENT DOCUMENTS

| | | | | |
|---|---|---|---|---|
| 5,197,895 | A * | 3/1993 | Stupecky | H01R 13/005 604/905 |
| 5,660,567 | A * | 8/1997 | Nierlich | H01R 29/00 439/620.21 |
| 5,865,801 | A * | 2/1999 | Houser | A61B 5/036 607/101 |
| 7,481,664 | B1 * | 1/2009 | Knoll | H01R 13/6275 439/359 |
| 7,720,521 | B2 | 5/2010 | Chang et al. | |
| 10,631,890 | B2 | 4/2020 | Palushi et al. | |
| 2003/0212384 | A1 * | 11/2003 | Hayden | A61M 29/02 604/533 |
| 2007/0060908 | A1 * | 3/2007 | Webster | A61B 17/22 604/509 |
| 2009/0177186 | A1 * | 7/2009 | Delano | A61M 39/1011 604/534 |
| 2014/0364725 | A1 | 12/2014 | Makower | |
| 2016/0008083 | A1 | 1/2016 | Kesten et al. | |
| 2018/0085174 | A1 | 3/2018 | Radtke et al. | |
| 2018/0310886 | A1 | 11/2018 | Salazar et al. | |
| 2018/0344978 | A1 | 12/2018 | Shameli et al. | |
| 2019/0167351 | A1 | 6/2019 | Salazar et al. | |
| 2019/0175282 | A1 | 6/2019 | Akbarian et al. | |
| 2019/0192176 | A1 | 6/2019 | Palushi et al. | |
| 2019/0374129 | A1 | 12/2019 | Palushi et al. | |

OTHER PUBLICATIONS

U.S. Appl. No. 62/741,594, entitled "Hollow Tube Surgical Instrument with Single Axis Sensor," filed Oct. 5, 2018.
U.S. Appl. No. 62/741,614, entitled "Dilation Instrument with Malleable Guide and Dilation Catheter with Integral Position Sensor," filed Oct. 5, 2018.
U.S. Appl. No. 62/741,778, entitled "Pointer Instrument with Malleable Shaft and Integral Position Sensor," filed Oct. 5, 2018.
U.S. Appl. No. 62/765,168, entitled "Endoscope with Anatomy Elevation Assembly," filed Aug. 17, 2018.
U.S. Appl. No. 62/777,799, entitled "Nasal Suction Instrument with Interchangeable Tip Insert," filed Dec. 11, 2018.

* cited by examiner

CONNECTOR TO COUPLE SURGICAL INSTRUMENT WITH NAVIGATION SYSTEM

PRIORITY

This application claims priority to U.S. Patent App. No. 62/780,384, entitled "Connector to Couple Surgical Instrument with Navigation System," filed Dec. 17, 2018, the disclosure of which is incorporated by reference herein.

BACKGROUND

In some instances, it may be desirable to operate within or adjacent to an anatomical passageway of a patient, such as performing an incision of mucosa, removal of bone, or dilation of an anatomical passageway. Such operations may occur within anatomical passageways such as ostia of paranasal sinuses (e.g., to treat sinusitis), the larynx, the Eustachian tube, or other passageways within the ear, nose, or throat, etc. In addition to the above described operations, or similar operations, it may be desirable to apply suction and/or irrigation within or adjacent to an anatomical passageway before, during, or after the above described operations, or similar operations. One method of applying suction within or adjacent to an anatomical passageway of a patient involves obtaining a suction device having an elongate shaft defining a lumen terminating at an open distal end of the elongated shaft, where the lumen is in fluid communication with an external suction source. An operator may then insert the distal end of the elongate shaft within the nostril or mouth of a patient toward a desired location within the patient. With the distal end of the elongate shaft inserted within the patient, an operator may manipulate the suction device and/or suction source in order to remove extraneous and/or undesired matter near or within an anatomical passageway of a patient. Applying suction and/or irrigation during an operation may be beneficial for multiple purposes as will be apparent to those skilled in the art.

Image-guided surgery (IGS) is a technique in which a computer is used to obtain a real-time correlation of the location of an instrument that has been inserted into a patient's body to a set of preoperatively obtained images so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a system display device (e.g., a video monitor) along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

It may be desirable to provide features that further facilitate the use of an IGS navigation system and associated components in ENT procedures and other medical procedures. While several systems and methods have been made and used with respect to IGS and ENT surgery, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
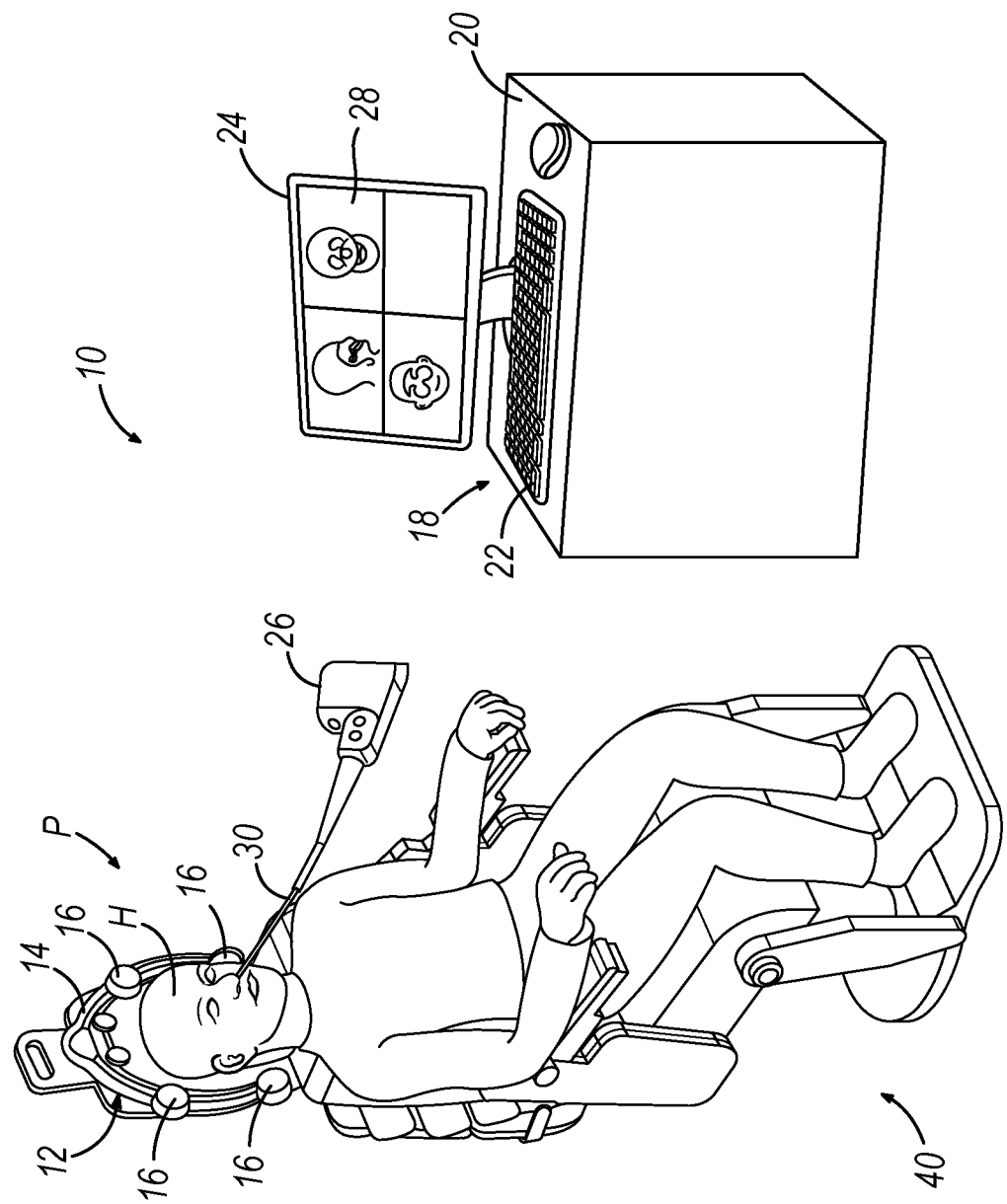
FIG. 1 depicts a schematic view of an exemplary sinus surgery navigation system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges are intended to encompass the exact value(s) referenced as well as a suitable dimensional tolerance that allows the part or collection of components to function for its intended purpose as described herein.

I. Exemplary Image Guided Surgery Navigation System

When performing a medical procedure within a head (H) of a patient (P), it may be desirable to have information regarding the position of an instrument within the patient's head (H), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (12), which comprises magnetic field generators (16) that are integrated into a horseshoe-shaped frame (14). Field generators (16) are operable to generate alternating magnetic fields of different frequencies around the head (H) of the patient (P). A navigation guidewire (30) is inserted into the head (H) of the patient (P) in this example. Navigation guidewire (30) may be a standalone device or may be positioned on an end effector or other location of a medical instrument such as a surgical cutting instrument or dilation instrument. In the present example, frame (14) is mounted to a chair (40), with the patient (P) being seated in the chair (40) such that frame (14) is located adjacent to the head (H) of the patient (P). By way of example only, chair (40) and/or field generator assembly (12) may be configured and operable in accordance with at least some of the teachings of U.S. Pub. No. 2018/0310886, entitled "Apparatus to Secure Field Generating Device to Chair," published Nov. 1, 2018, issued as U.S. Pat. No. 10,561,370 on Feb. 18, 2020, the disclosure of which is incorporated by reference herein.

IGS navigation system (10) of the present example further comprises a processor (18), which controls field generators (16) and other elements of IGS navigation system (10). For instance, processor (18) is operable to drive field generators (16) to generate alternating electromagnetic fields; and process signals from navigation guidewire (30) to determine the location of a sensor in navigation guidewire (30) within the head (H) of the patient (P). Processor (18) comprises a processing unit communicating with one or more memories. Processor (18) of the present example is mounted in a console (20), which comprises operating controls (22) that include a keypad and/or a pointing device such as a mouse or trackball. A physician uses operating controls (22) to interact with processor (18) while performing the surgical procedure.

Navigation guidewire (30) includes a sensor (not shown) that is responsive to positioning within the alternating magnetic fields generated by field generators (16). A coupling unit (26) is secured to the proximal end of navigation guidewire (30) and is configured to provide communication of data and other signals between console (20) and navigation guidewire (30). Coupling unit (26) may provide wired or wireless communication of data and other signals between console (20) and navigation guidewire (30).

In the present example, the sensor of navigation guidewire (30) comprises at least one electrically conductive coil at the distal end of navigation guidewire (30). When such a coil is positioned within an alternating electromagnetic field generated by field generators (16), the alternating magnetic field may generate electrical current in the coil, and this electrical current may be communicated proximally along the electrical conduit(s) in navigation guidewire (30) and further to processor (18) via coupling unit (26). This phenomenon may enable IGS navigation system (10) to determine the location of the distal end of navigation guidewire (30) or other medical instrument (e.g., dilation instrument, surgical cutting instrument, etc.) within a three-dimensional space (i.e., within the head (H) of the patient (P), etc.). To accomplish this, processor (18) executes an algorithm to calculate location coordinates of the distal end of navigation guidewire (30) from the position related signals of the coil(s) in navigation guidewire (30). While the position sensor is located in guidewire (30) in this example, such a position sensor may be integrated into various other kinds of instruments, including those described in greater detail below.

Processor (18) uses software stored in a memory of processor (18) to calibrate and operate IGS navigation system (10). Such operation includes driving field generators (16), processing data from navigation guidewire (30), processing data from operating controls (22), and a driving display screen (24). In some implementations, operation may also include monitoring and enforcement of one or more safety features or functions of IGS navigation system (10). Processor (18) is further operable to provide video in real time via display screen (24), showing the position of the distal end of navigation guidewire (30) in relation to a video camera image of the patient's head (H), a CT scan image of the patient's head (H), and/or a computer-generated three-dimensional model of the anatomy within and adjacent to the patient's nasal cavity. Display screen (24) may display such images (28) simultaneously and/or superimposed on each other during the surgical procedure. Such displayed images (28) may also include graphical representations of instruments that are inserted in the patient's head (H), such as navigation guidewire (30), such that the operator may view the virtual rendering of the instrument at its actual location in real time. By way of example only, display screen (24) may provide images (28) in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (24).

The images (28) provided through display screen (24) may help guide the operator in maneuvering and otherwise manipulating instruments within the patient's head (H) when such instruments incorporate navigation guidewire (30). It should also be understood that other components of a surgical instrument and other kinds of surgical instruments, as described below, may incorporate a sensor like the sensor of navigation guidewire (30).

II. Exemplary Navigable Suction Instrument

Various surgical procedures may warrant the use of a suction instrument in order to clear fluids and/or debris from the surgical field and/or from other sites within a patient. For instance, suction may be desirable in FESS procedures, sinuplasty procedures, and/or in various other ENT procedures. Furthermore, in some instances, it may be desirable to provide image guided navigation capabilities to such a suction instrument.

Figure 2:
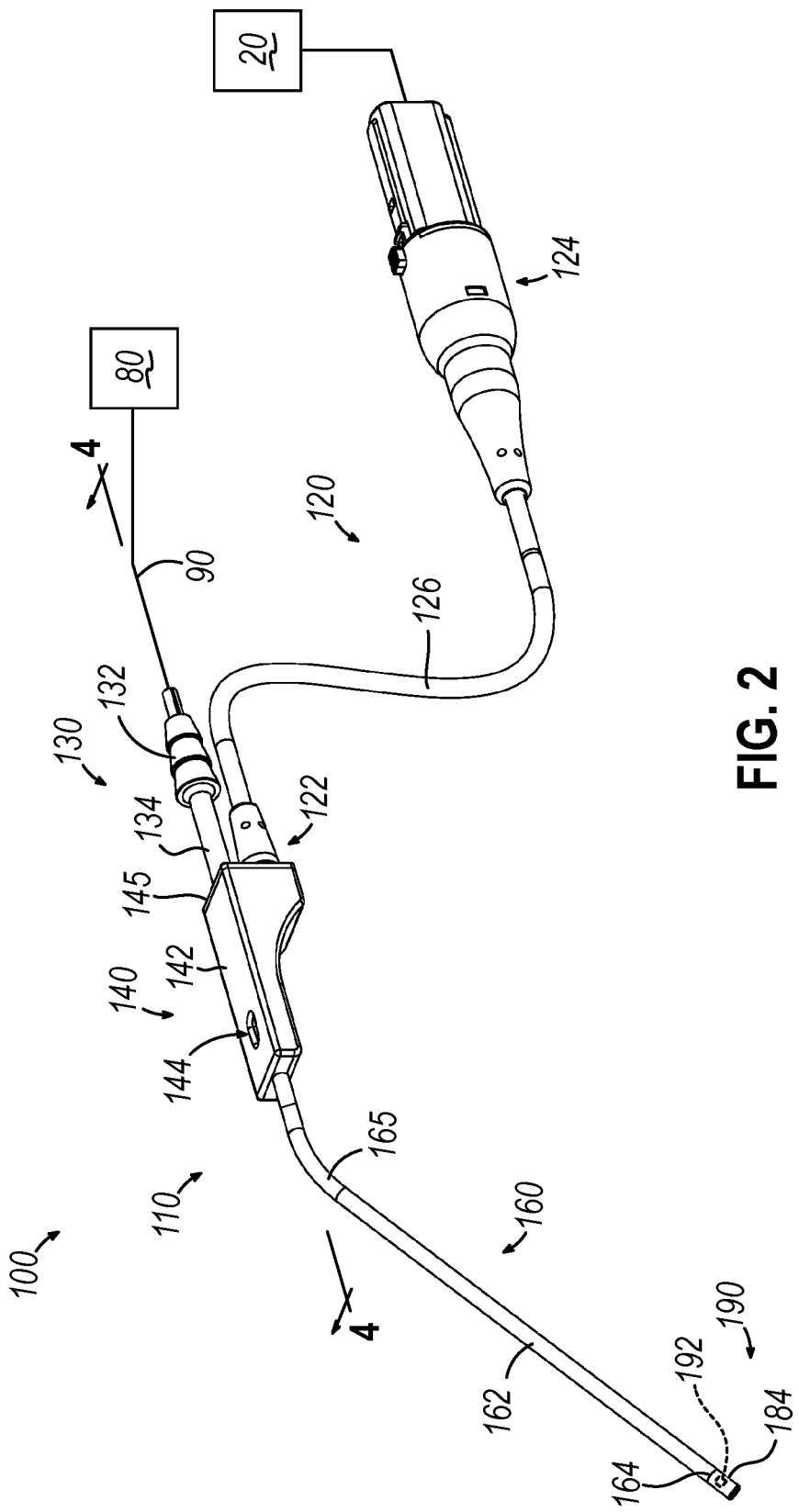
FIG. 2 depicts a perspective view of an exemplary assembly having a suction instrument and a cable assembly for coupling the suction instrument with the navigation system of FIG. 1.

FIG. 2 shows an exemplary suction instrument assembly (100) operable to provide suction during surgical procedures, and which is configured for use with IGS navigation system (10) described above. Suction instrument assembly (100) includes a suction instrument (110) that is fluidly coupled with a suction source (80) via a suction conduit (90). Suction source (80) may comprise a vacuum pump and a fluid reservoir, among other components readily apparent to persons of ordinary skill in the art, and is configured to provide enough suction at a surgical site to pull excess fluid and/or debris proximally through suction instrument (110).

Figure 3:
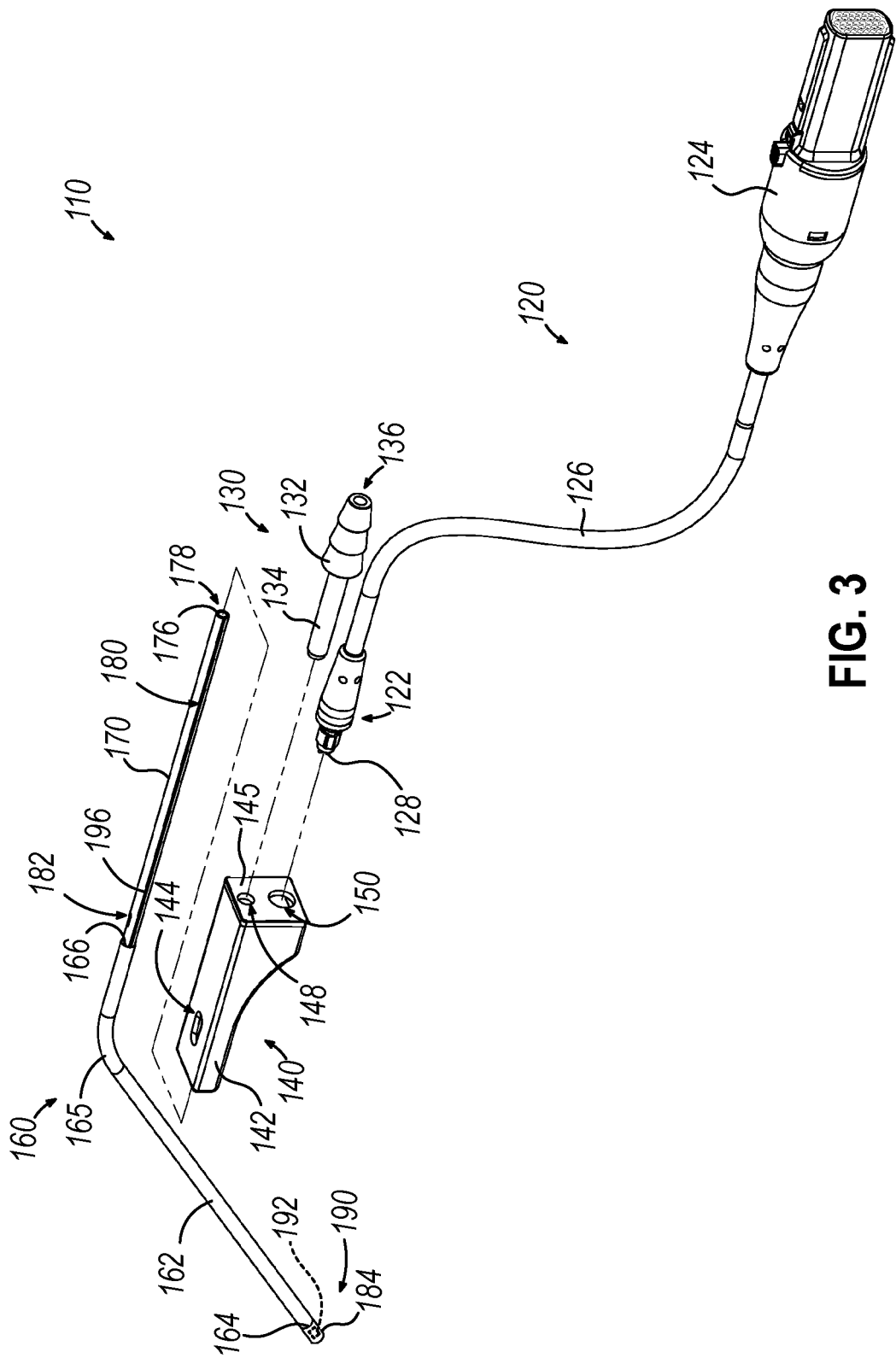
FIG. 3 depicts an exploded perspective view of the suction instrument of FIG. 2.

As best seen in FIGS. 2 and 3, suction instrument (110) includes a coupling unit (120), a proximal suction conduit port (130), a grip portion (or "handle assembly") (140), and an elongate cannula assembly (160). A distal end of cannula assembly (160) is configured to be inserted, transnasally or otherwise, within or adjacent to a nasal cavity of a patient (or elsewhere within a patient) to provide suction at a selected surgical site. Cannula assembly (160) includes a sensor assembly (190) mounted at a distal end thereof. As described below, sensor assembly (190) includes a navigation sensor (192) (shown schematically) operable to communicate signals to console (20) of IGS navigation system (10) via a coupling unit (120). Based on these signals, processor (18) may execute an algorithm to determine a 3-dimensional spatial location of the distal end of cannula assembly (160) relative to the anatomy of patient (P).

Coupling unit (120) is in the form of a cable assembly having a sensor coupling (122), a console coupling (124), and a cable (126) connecting and establishing communication between sensor coupling (122) and console coupling (124). Sensor coupling (122) includes prongs (128) that are housed within a proximal cavity (156) of grip portion (140). Console coupling (124) is configured to couple with console (20), and sensor coupling (122) is configured to couple with sensor assembly (190) of suction instrument (110), such that sensor assembly (190) is in communication with console (20). Console coupling (124) may be in wired or wireless communication with console (20), similar to coupling unit (26) described above. Additionally, coupling unit (120) may be configured to communicate data or other signals unidirectionally or bi-directionally between suction instrument (110) and console (20).

Proximal suction conduit port (130) includes a proximal barbed portion (132), a distal shaft (134), and an internal pathway (136). Proximal barbed configuration (132) is configured to provide a secure fit with suction conduit (90) such that pathway (136) and the interior of suction conduit (90) are in fluid communication with each other.

Figure 4:
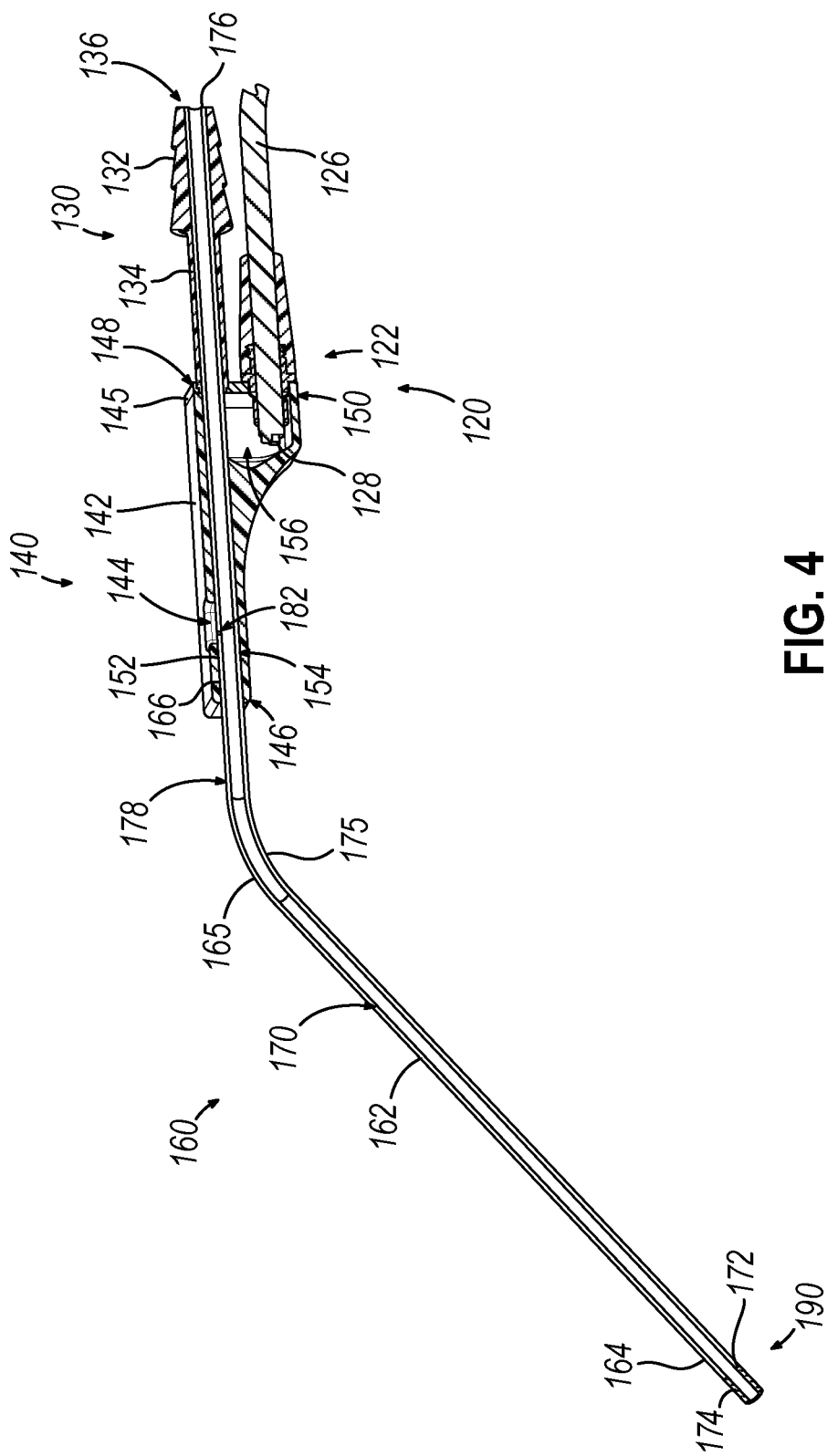
FIG. 4 depicts a cross-sectional perspective view of the suction instrument of FIG. 2, taken along line 4-4 of FIG. 2.
Figure 5:
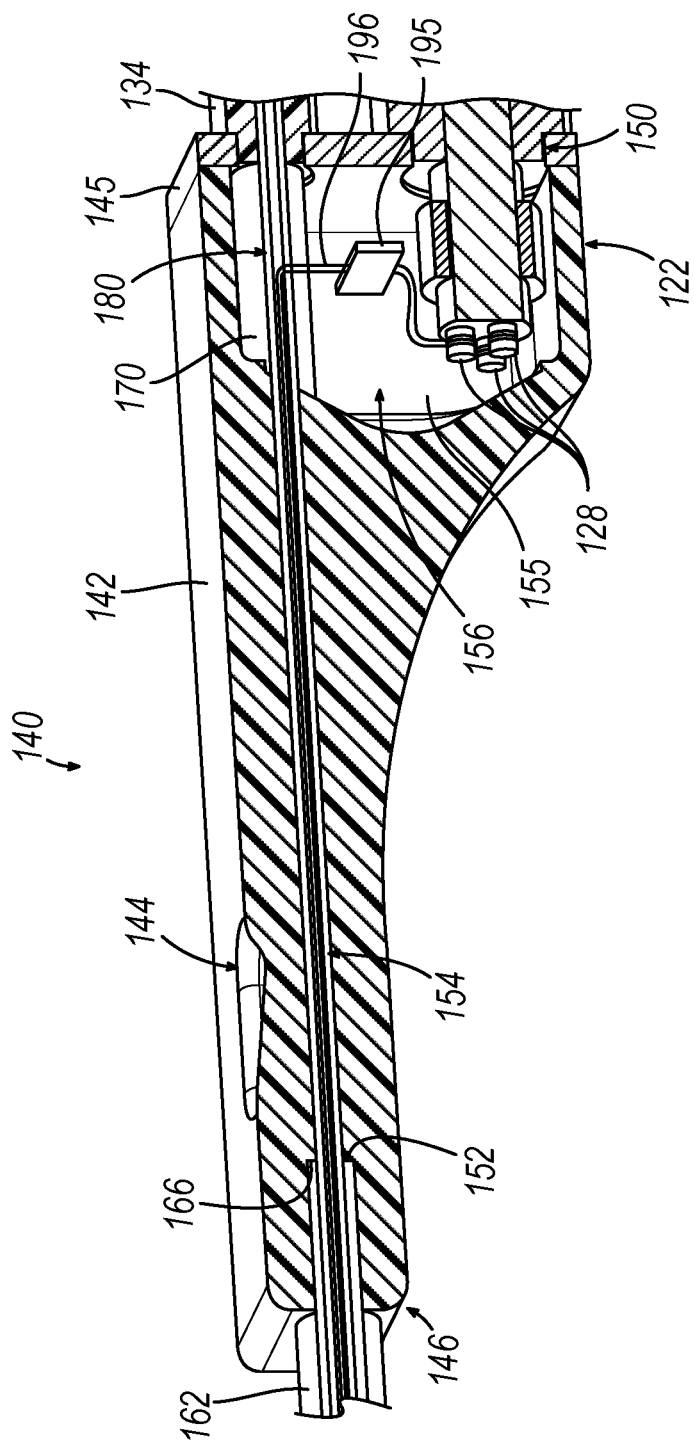
FIG. 5 depicts a cross-sectional perspective view of a handle assembly of the suction instrument of FIG. 2.

As shown in FIGS. 2-5, grip portion (140) includes a body (142) and a proximal cap (145). Body (142) may be grasped by an operator such that the operator may manipulate and control suction instrument (110). Body (142) defines a first vent opening (144), a distal opening (146), proximal cavity (156), and a pathway (154) that extends from distal opening (146) into proximal cavity (156). Proximal cap (145) attaches to a proximal portion of body (142) and closes proximal cavity (156). Proximal cap (145) includes a first proximal opening (148) that receives shaft (134) of proximal suction conduit port (130), and a second proximal opening (150) that receives sensor coupling (122) of coupling unit (120). As shown in FIG. 5, pathway (154) includes a distally presented shoulder (152) configured to abut an open proximal end (166) of an external sheath (162) of cannula assembly (160) when inserted proximally through distal opening (146) during assembly.

Elongate cannula assembly (160) includes an external sheath (162), an interior suction tube (170), a sensor assembly (190), and a distal cap (184) covering sensor assembly (190). External sheath (162) extends from an open distal end (164) to an open proximal end (166), with a bent portion (165) located therebetween. External sheath (162) defines a hollow interior that houses a portion of interior suction tube (170) as well as a portion of a communication wire (196) extending within and along a guided path (180) defined by interior suction tube (170).

Interior suction tube (170) extends from an open distal end (174) to an open proximal end (176), with a bent portion (175) located therebetween. As shown in FIG. 4, interior suction tube (170) includes a narrowed distal portion (172) that extends distally of open distal end (164) of external sheath (162) and through sensor assembly (190), such that sensor assembly (190) is fixed to narrowed distal portion (172). As shown in FIG. 3, interior suction tube (170) defines a guided path (180) that houses communication wire (196) extending proximally from sensor assembly (190), in cooperation with external sheath (162). Suction tube (170) and external sheath (162) may be rigid and configured to maintain the bend of bent portions (165, 175) without buckling during insertion into a patient's nasal cavity.

As shown in FIG. 4, interior suction tube (170) defines a suction lumen (178) that extends from open distal end (174) to open proximal end (176). A proximal portion of interior suction tube (170) is received through distal opening (146) of grip portion body (142) and extends proximally into pathway (136) of suction conduit port (130), such that suction lumen (178) is configured to fluidly couple with suction source (80) via suction conduit (90). As shown in FIGS. 3 and 4, first vent opening (144) of grip portion (140) fluidly communicates with suction lumen (178) through a second vent opening (182) formed in suction tube (170). During operation, an operator may grasp grip portion (140) and selectively close first vent opening (144) to communicate suction from suction source (80) to suction lumen (178). As shown, first vent opening (144) may be formed with a teardrop shape (or some other elongate shape) to enable the operator to selectively vary the amount of suction communicated from suction source (80) to suction lumen (178) based on the longitudinal position of the operator's thumb (or other finger) on first vent opening (144).

In some instances, suction source (80) remains in a constantly activated state throughout a surgical procedure. In such instances, the operator may leave first vent opening (144) uncovered while positioning open distal end (174) of instrument (110) within the patient such that suction source (80) draws suction through vent openings (144, 182) rather than through open distal end (174). When the operator wishes to apply suction to a target surgical site within the patient via open distal end (174), the operator at least partially covers vent opening (144) with a thumb, finger, or other object, so that suction is then communicated from suction source (80) to open distal end (174).

Navigation sensor (192) of sensor assembly (190) mounted at the distal end of cannula assembly (160) may comprise an annular sensor in accordance with the teachings of U.S. patent application Ser. No. 15/964,886, entitled "Navigable Suction Instrument with Coaxial Annular Sensor," filed Apr. 27, 2018, issued as U.S. Pat. No. 11,253,677 on Feb. 22, 2022, the disclosure of which is incorporated by reference herein. Navigation sensor (192) may include one or more electrically conductive members such as coils, layers of wire windings, etc. in which an electrical current is induced in response to presence of sensor assembly (190) within an electromagnetic field generated by field generators (16) of IGS navigation system (10). One or more sensor wires (not shown) extend proximally from sensor assembly (190) through cannula assembly (160) and couple with communication wire (196), which extends along guided path (180) into proximal cavity (156) of grip portion (140), as shown in FIG. 5. Communication wire (196) is coupled with a PCB board (195) that in turn couples with prongs (128) of sensor coupling (122). As described above, coupling unit (120) is configured to communicate with console (20) of IGS navigation system (10).

Electrical currents induced within navigation sensor (192) are transmitted as electrical signals proximally through the sensor wires to communication wire (196), through PCB board (195), and to coupling unit (120), which communicates the signals to console (20) of IGS navigation system (10). Processor (18) then executes an algorithm to calculate 3-dimensional location coordinates of navigation sensor (192) based on the received electrical signals. Because sensor assembly (190) is fixed at the distal end (174) of elongate cannula assembly (160), IGS navigation system (10) may thus calculate, track, and display the location of at least the distal end within the patient (P) in real time during a surgical procedure. While tracking the location of cannula assembly (160) within patient (P), an operator may selectively apply suction at any suitable time in accordance with the teachings above. It will be appreciated that suction instrument assembly (100) may be further configured and operable in accordance with one or more teachings of U.S. patent application Ser. No. 15/964,886, issued as U.S. Pat. No. 11,253,677 on Feb. 22, 2022, incorporated by reference above.

III. Exemplary Alternative Cable Assembly Having Rectangular Distal Coupling

As shown in FIGS. 2-4, described above, distal coupling (122) of cable assembly (120) is configured with a generally circular cross-section and thus circular symmetry about its longitudinal axis. An exterior of distal coupling (122) may be provided with indicia to facilitate proper rotational alignment (or "indexing") of distal coupling (122) relative to grip portion (140) of suction instrument (110) via visual inspection by the operator, such that the electrical connectors of instrument (110) and distal coupling (122) may be successfully connected. In some instances, it may be desirable to provide distal coupling (122) with an alternative configuration that promotes quick and effective indexing relative to suction instrument (110) with little to no visualization by the operator required. Such a configuration may be desirable in low-light surgical applications, for example, where it may be difficult for an operator to visually identify the rotational orientation of distal coupling (122) relative to suction instrument (110) before coupling the two components together. The following description provides a merely illustrative example of how distal coupling (122) may be alternatively configured in such a manner.

A. Overview of Cable Assembly Having Rectangular Distal Coupling

Figure 6:
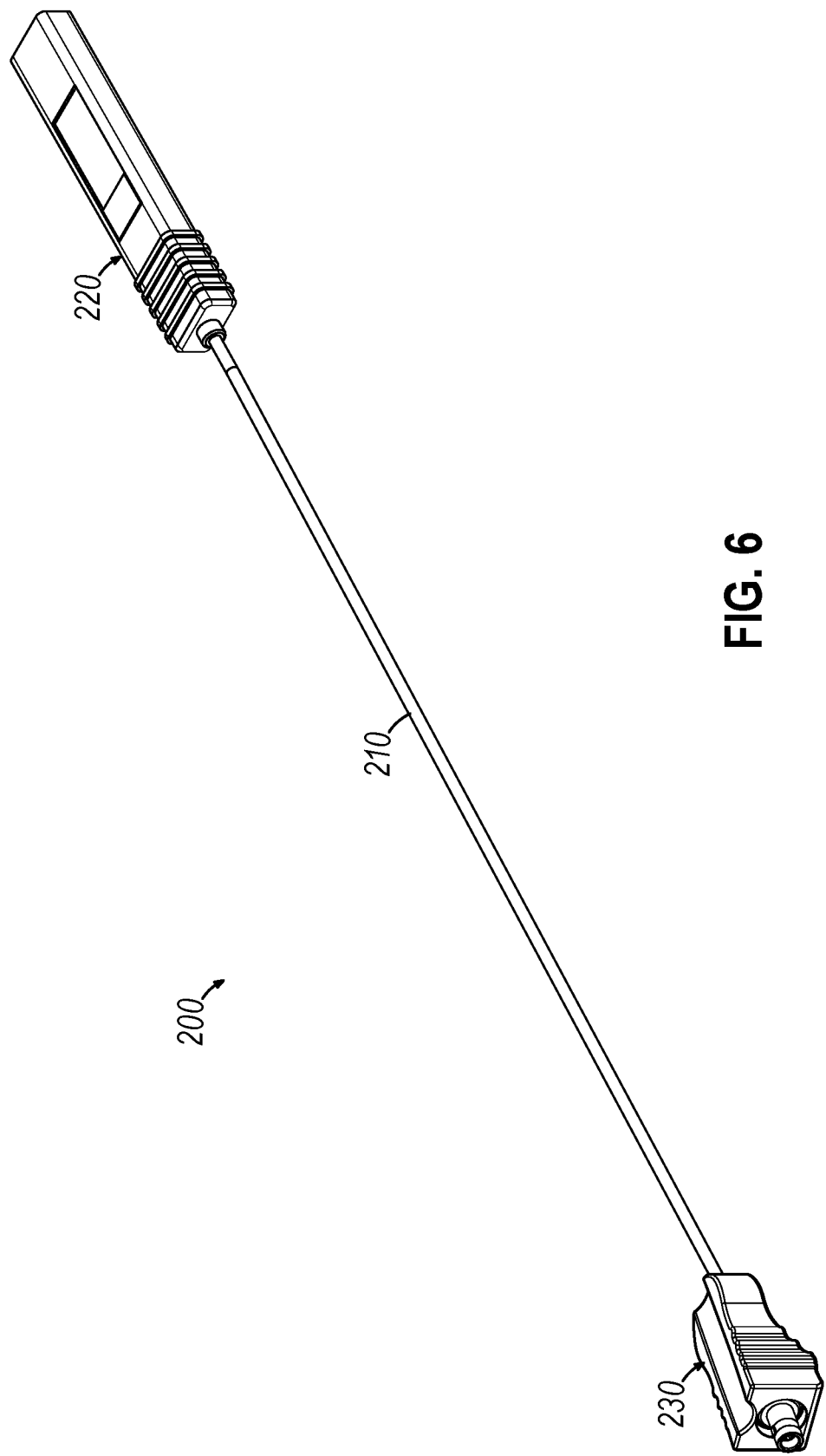
FIG. 6 depicts a perspective view of another exemplary cable assembly suitable for coupling a surgical instrument with the surgical navigation system of FIG. 1.

FIG. 6 shows an exemplary alternative coupling unit in the form of cable assembly (200), which is configured to couple a navigable suction instrument (300) (see FIG. 9) with IGS navigation system (10) so that a navigation sensor of suction instrument (300) may communicate with processor (18) of navigation system (10). Cable assembly (200) includes a cable (210), a proximal coupling (220) disposed at a proximal end of cable (210), and a distal coupling (230) disposed at a distal end of cable (210). Cable (210) of the present example connects and establishes communication between proximal coupling (220) and distal coupling (230) via one or more electrically conductive members (e.g., wires) housed within cable (210). Proximal coupling (220) is configured to releasably couple with a component (e.g., an adapter or hub) of navigation system (10) that is in communication with processor (18) via a wired or wireless connection. Distal coupling (230) is configured to releasably couple with a proximal end of suction instrument (300), as described in greater detail below.

In alternative versions of cable assembly (200), cable (210) may establish communication between proximal and distal couplings (220, 230) via energy transmission members configured to transmit non-electrical energy signals, such as optical fibers, for example. In such versions, proximal and distal couplings (220, 230) may be suitably configured to facilitate connection of such energy transmission members to respective devices and/or systems being coupled via cable assembly (200). In that regard, while cable assembly (200) is shown and described in connection with navigation system (10) and suction instrument (300), it will be appreciated that cable assembly (200) may be employed with various other types of systems and devices. By way of example only, such devices may include any one or more of the type disclosed in U.S. Pub. No. 2018/0085174, entitled "Suction Device for Use in Image-Guided Sinus Medical Procedure," published Mar. 29, 2018, now abandoned; U.S. App. No. 62/658,688, entitled "Curette with Navigation Sensor," filed Mar. 17, 2018; U.S. application Ser. No. 15/795,473, entitled "Tissue Shaving Instrument," filed Oct. 27, 2017, issued as U.S. Pat. No. 10,631,890 on Apr. 28, 2020; U.S. application Ser. No. 15/830,205, entitled "Dilation Instrument with Navigation and Distally Located Force Sensor," filed Dec. 4, 2017, issued as U.S. Pat. No. 10,864,046 on Dec. 15, 2020; U.S. application Ser. No. 15/839,274, entitled "Tissue Shaving Instrument with Navigation Sensor," filed Dec. 12, 2017, issued as U.S. Pat. No. 10,959,785 on Mar. 30, 2021; U.S. application Ser. No. 15/852,470, entitled "Dilation Instrument with Guide Catheter Type Sensor," filed Dec. 22, 2017, now abandoned; U.S. application Ser. No. 16/002,016, entitled "Endoscope with Integral Navigation Sensor," filed Jun. 7, 2018, publisded as U.S. Pub. No. 2019/0374129 on Dec. 12, 2019; U.S. App. No. 62/765,168, entitled "Endoscope with Anatomy Elevation Assembly," filed Aug. 17, 2018; U.S. App. No. 62/741,594, entitled "Hollow Tube Surgical Instrument with Single Axis Sensor," filed Oct. 5, 2018; U.S. App. No. 62/741,614, entitled "Dilation Instrument with Malleable Guide and Dilation Catheter with Integral Position Sensor," filed Oct. 5, 2018; or U.S. App. No. 62/741,778, entitled "Pointer Instrument with Malleable Shaft and Integral Position Sensor," filed Oct. 5, 2018; the disclosures of these references being incorporated by reference herein.

Figure 9:
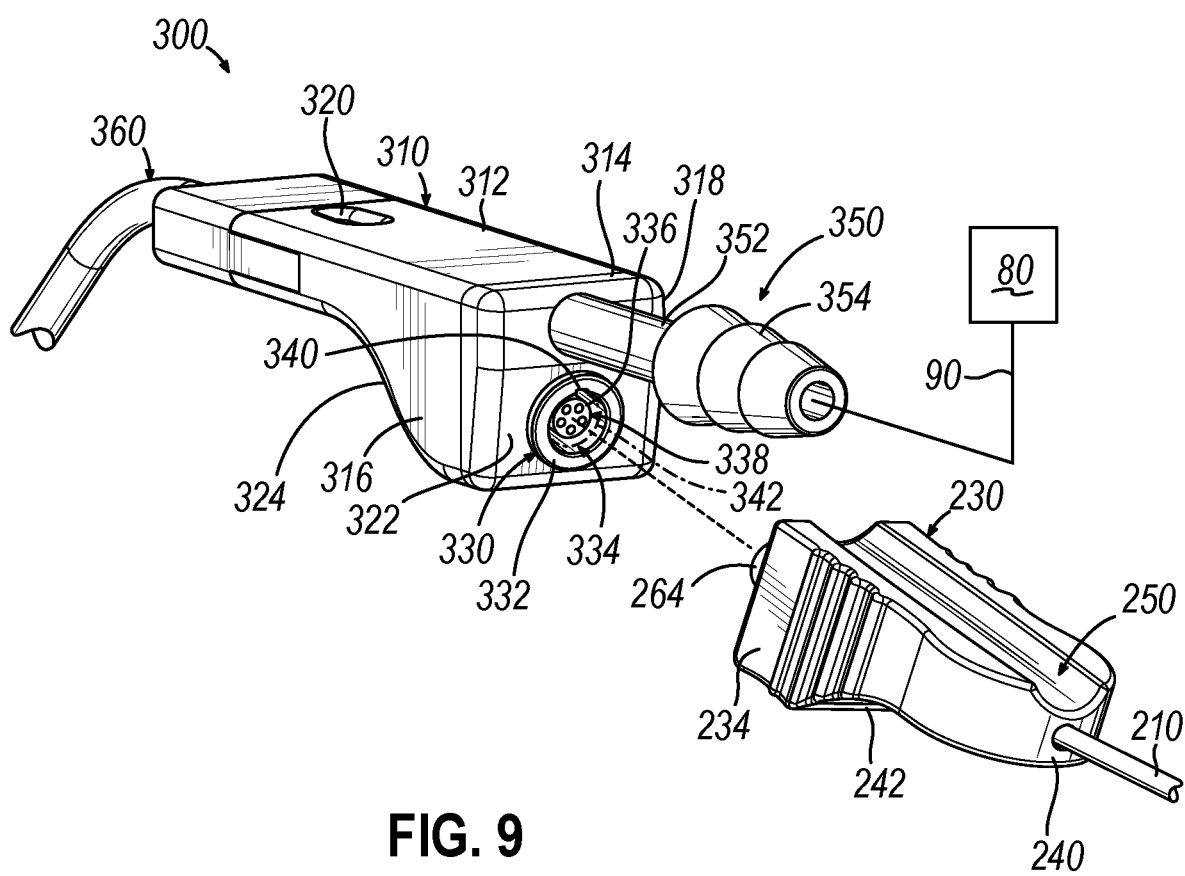
FIG. 9 depicts a disassembled perspective view of the distal coupling of FIG. 7 and a suction instrument, showing an electrical connector of the distal coupling being aligned with an electrical connector of the suction instrument.

Suction instrument (300) is generally similar to suction instrument (110) described above, except as otherwise described below. As shown in FIG. 9, suction instrument (300) includes a grip portion (310) and an elongate cannula assembly (360) extending distally from grip portion (310). Grip portion (310) includes a body (312) defining an interior cavity (not shown), and a proximal cap (314) coupled to a proximal end of body (312). Body (312) of the present version extends longitudinally along a body axis and has a generally rectangular cross-section transverse to the body axis that defines opposed first and second lateral sides (316, 318) extending parallel to one another. A suction conduit port (350) extends proximally from an upper portion of proximal cap (314) along the body axis and fluidly communicates with an internal suction passage (not shown) extending longitudinally through body (312), which fluidly communicates with an internal suction lumen (not shown) of cannula assembly (360). Suction conduit port (350) includes a proximal shaft portion (352) and a distal barbed portion (354) configured to couple with suction conduit (90) to establish fluid communication between suction source (80) and the suction lumen. A vent opening (320) extends through an upper surface of grip portion body (312) and fluidly communicates with the internal suction passage of body (312) and thus the suction lumen of cannula assembly (360). In some versions, a distal end of grip portion (310) may be configured to releasably couple and decouple from a proximal end of cannula assembly (360) in the manner disclosed in U.S. App. No. 62/777,799, entitled "Nasal Suction Instrument with Interchangeable Tip Insert," filed Dec. 11, 2018, the disclosure of which is incorporated by reference herein.

Grip portion (310) of suction instrument (300) further comprises an electrical connector (330) that is housed within a proximal portion of body (312) and is exposed through a planar proximal face (322) of a lower portion of proximal cap (314). Electrical connector (330) is electrically coupled with a navigation sensor (not shown) mounted at a distal end of cannula assembly (360). The navigation sensor may be configured and operable similar to navigation sensor (192) of suction instrument (110) described above. Electrical connector (330) of the present version includes an annular rim (332) disposed on planar proximal face (322), and a connector socket (334) that extends into body (312) through proximal cap (314). Connector socket (334) houses a cylindrical contact body (336), which houses a plurality of electrical contacts (e.g., five) in the form of contact sockets (338). As described in greater detail below, electrical connector (330) is configured to electrically couple with an electrical connector (260) of distal coupling (230) of cable assembly (200) so that the navigation sensor of cannula assembly (360) may communicate with processor (18) of IGS navigation system (10) through cable assembly (200).

Figure 7:
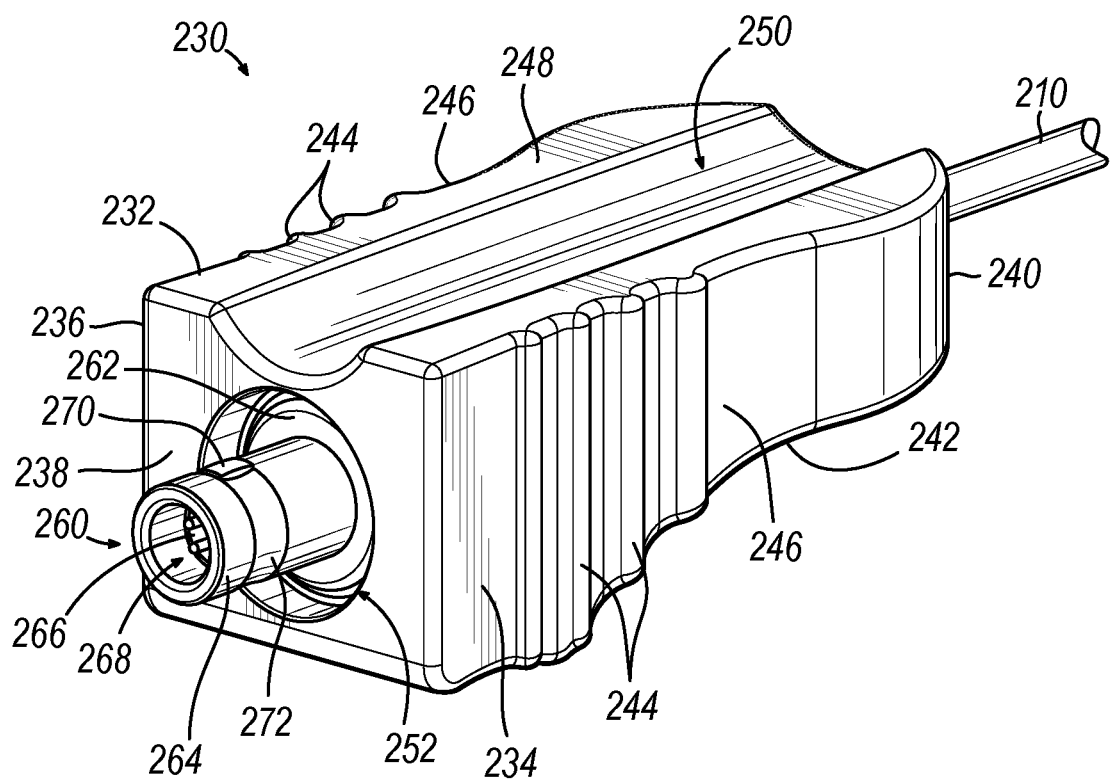
FIG. 7 depicts a perspective view of a distal coupling of the cable assembly of FIG. 6.
Figure 8:
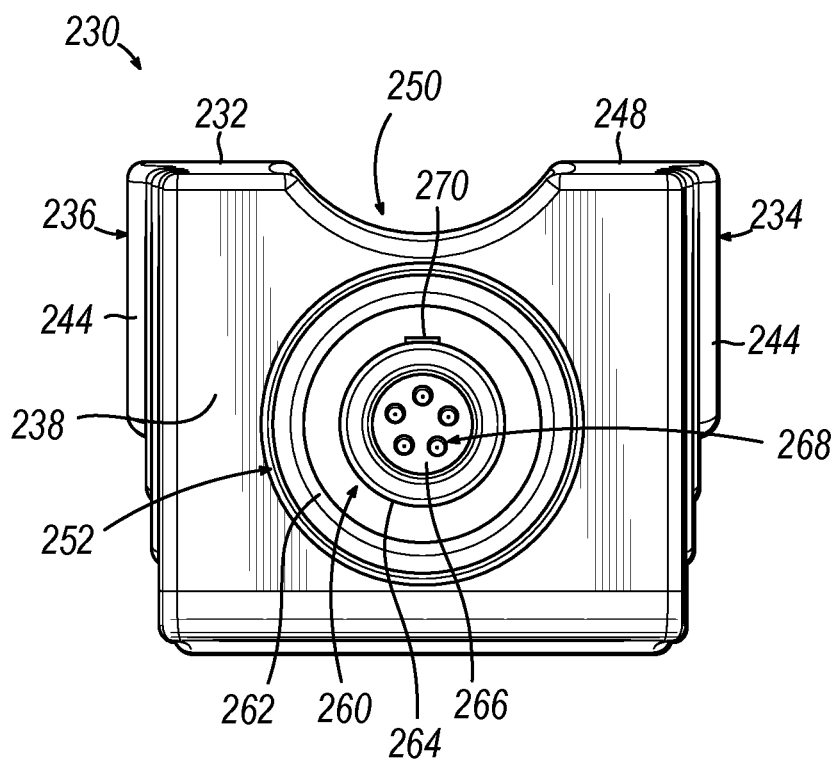
FIG. 8 depicts a distal end elevational view of the distal coupling of FIG. 7.

As shown in FIGS. 7 and 8, distal coupling (230) of cable assembly (200) comprises a coupling body (232) and an electrical connector (260), which is housed within an interior of coupling body (232) and is exposed through a distal opening (252) of coupling body (232). A distal end of cable (210) extends distally into the interior of coupling body (232) and is electrically coupled with a base (262) of electrical connector (260) therein. Coupling body (232) of the present version extends longitudinally along a coupling axis with a generally rectangular cross-section transverse to the coupling axis that defines opposed first and second lateral sides (234, 236) extending parallel to one another. Coupling body (232) has a planar distal face (238), a rounded proximal end (240), and a proximal portion that tapers proximally toward rounded proximal end (240) to define a concavely contoured bottom surface (242) that extends between first and second lateral sides (234, 236). Each lateral side (234, 236) includes a gripping feature that comprises a plurality of ridges (244) arranged distally on the side (234, 236), and a concave depression (246) arranged proximally of ridges (244). Ridges (244) and concave depressions (246) are configured to facilitate secure gripping of distal coupling (230) by an operator. For instance, an operator may grasp distal coupling (230) along lateral sides (234, 236) between an index finger and a thumb. The operator may also position one or more other fingers (e.g., a middle finger) underneath coupling body (232), along concavely contoured bottom surface (242), to help stabilize distal coupling (230) during attachment and detachment of distal coupling (230) relative to suction instrument (300).

Coupling body (232) of distal coupling (230) further includes a top surface (248) having a recessed channel (250) formed therein. Recessed channel (250) has a generally semi-circular cross-sectional shape and extends longitudinally along the coupling axis from planar distal face (238) to rounded proximal end (240), such that recessed channel (250) is open at both of its longitudinal ends. As shown best in FIGS. 10A-10B, described in greater detail below, recessed channel (250) is formed with a lateral width and a transverse depth sufficient to enable recessed channel (250) to receive an underside of at least proximal shaft portion (352) of suction conduit port (350) therein, as well as a distal end of suction conduit (90) fitted over port (350).

It will be appreciated that recessed channel (250) and other features of distal coupling (230) may be suitably configured to promote receipt of any desired portion of suction conduit port (350) and the proximal end of suction conduit (90) into recessed channel (250). Moreover, the lateral width and transverse depth of recessed channel (250) may be constant or varied along a length of recessed channel (250). For instance, though not shown, the transverse depth of recessed channel (250) may taper proximally such that recessed channel (250) extends for only a partial length of coupling body (232) and is open at only its distal end. As shown in FIG. 10B, configuring distal coupling (230) to receive at least a portion of suction conduit port (350) and suction conduit (90) into recessed channel (250) provides the combined assembly with a slim profile that may be easily held and manipulated by the operator during a procedure.

As shown best in FIGS. 7 and 8, electrical connector (260) of distal coupling (230) comprises a base (262) housed within an interior of coupling body (232), and a tubular member (264) projecting distally from base (262) through distal opening (252). Tubular member (264) houses a cylindrical contact body (266), which houses a plurality of electrical contacts (e.g., five) in the form of contact pins (268) that project distally and are configured to be received by contact sockets (338) of electrical connector (330). In other versions, electrical connector (260) may comprise one or more contact sockets and electrical connector (330) may comprises one or more contact pins (268). A key (270) projects radially outwardly from a side surface of tubular member (264). Key (270) is configured to be slidably received by an axial keyway (340) formed in electrical connector (330) of suction instrument (300) when electrical connectors (260, 330) are rotationally aligned with one another, to ensure proper mating of contact pins (268) with contact sockets (338).

Electrical connector (260) of distal coupling (230) further includes an integrated first latch feature in the form of an annular groove (272) formed in the side surface of tubular member (264), in axial alignment with key (270). Annular groove (272) is configured to releasably capture a corresponding second latch feature (342) (shown schematically in FIG. 9) integrated into connector socket (334) of electrical connector (330) when distal coupling (230) is fully coupled with grip portion (310). By way of example only, second latch feature (342) may comprise an annular rim, a resilient boss, a ball detent, or various other suitable features configured to be releasably captured by annular groove (272) upon full distal insertion of tubular member (264) into connector socket (334). This releasable engagement of latch features (272, 342) lockingly couples distal coupling (230) with grip portion (310) to prevent unintended separation of distal coupling (230) from grip portion (310), while still permitting intentional separation of distal coupling (230) from grip portion (310) when desired. While latch features (272, 342) of the present example are integrated into electrical connectors (260, 330), it will be appreciated that they may be provided on various other portions of grip portion (310) and distal coupling (230) in other examples.

FIGS. 9-10B show distal coupling (230) of cable assembly (200) being coupled with the proximal end of grip portion (310) of suction instrument (300). An operator may grasp suction instrument (300) with one hand and distal coupling (230) with the other hand. In particular, as described above, the operator may grasp first and second lateral sides (234, 236) of distal coupling (230) between an index finger and a thumb, while positioning one or more additional fingers (e.g., a middle finger) underneath grip portion body (312), along concavely contoured bottom surface (242). The operator may grasp grip portion (310) of suction instrument (300) in a similar manner with the other hand. The operator may then rotationally manipulate distal coupling (230) and/or grip portion (310) so that first and second lateral sides (234, 236) of distal coupling (230) are parallel with first and second lateral sides (316, 318) of grip portion (310). Such an orientation aligns key (270) of distal coupling (230) with keyway (340) of grip portion (310), such that tubular member (264) of distal coupling electrical connector (260) may be successfully inserted into connector socket (334) of grip portion electrical connector (330).

The rectangular profiles of distal coupling (230) and grip portion (310), which define the parallel sets of lateral sides (234, 236, 316, 318), enable the operator to quickly and easily achieve proper rotational indexing tactilely, with little to no visualization of the features of grip portion (310) and distal coupling (230) being required. Gripping features (244, 246) provided on lateral sides (234, 236) distal coupling (230) enable the operator to easily grasp, index, connect, and disconnect distal coupling (230) relative to grip portion (310), even when wearing multiple sets of surgical gloves. Furthermore, distal coupling (230) of the present example is formed with a lateral width that is approximately equal to a lateral width of a proximal end of grip portion (310), such that lateral sides (234, 236) of distal coupling (230) are configured to align generally flush with lateral sides (316, 318) of grip portion (310), as shown in FIG. 10B. Such a configuration further facilitates an operator in quickly and properly indexing distal coupling (230) relative to grip portion (310) tactilely, with little to no visualization. As noted above, the ability to properly index distal coupling (230) relative to grip portion (310) with minimal visualization is particularly beneficial in low-light surgical applications, where visualization of printed indicia or other features relied upon by an operator for properly indexing a coupling (e.g., having circular symmetry) is difficult or impossible.

After properly indexing distal coupling (230) relative to grip portion (310), the operator guides distal coupling (230) and grip portion (310) together axially to insert tubular member (264) of distal coupling electrical connector (260) into connector socket (334) of grip portion electrical connector (330). Tubular member (264) is received within connector socket (334) such that key (270) slides distally into keyway (340), and such that contact body (336) of grip portion (310) is received into tubular member (264) to confront contact body (266) of distal coupling (230). Further distal advancement of distal coupling (230) relative to grip portion (310) causes contact pins (268) of distal coupling (230) to insert into contact sockets (338) of grip portion (310). Simultaneously, annular rim (332) of grip portion electrical connector (330) is received into an annular space that encircles tubular member (264) within distal opening (252) of coupling body (232). Additionally, suction conduit port (350) of grip portion (310) is received into at least a proximal portion of recessed channel (250) of distal coupling (230), as described above. Finally, as planar distal face (238) of distal coupling (230) confronts and abuts planar proximal face (322) of grip portion (310), latch features (272, 342) engage one another to releasably lock distal coupling (230) and grip portion (310) together.

The resulting configuration places suction instrument (300) in secure electrical communication with cable assembly (200), such that electrical signals generated by the navigation sensor of cannula assembly (360) may be communicated proximally from suction instrument (300) to cable assembly (200), and from cable assembly (200) to processor (18) of IGS navigation system (10). As described above in connection with suction instrument (110), such communication enables navigation system (10) to track and visually display a location of the distal end of cannula assembly (360) within patient (P) during a surgical procedure.

Figure 10A:
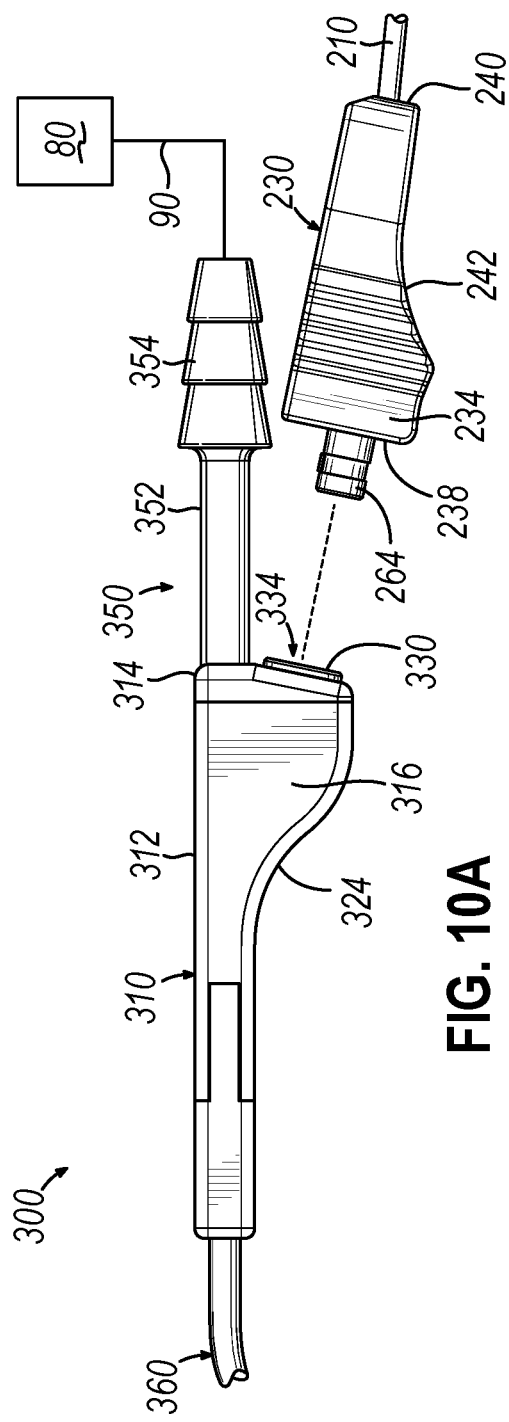
FIG. 10A depicts a disassembled side elevational view of the distal coupling and the suction instrument of FIG. 9, showing the electrical connector of the distal coupling aligned with the electrical connector of the suction instrument.
Figure 10B:
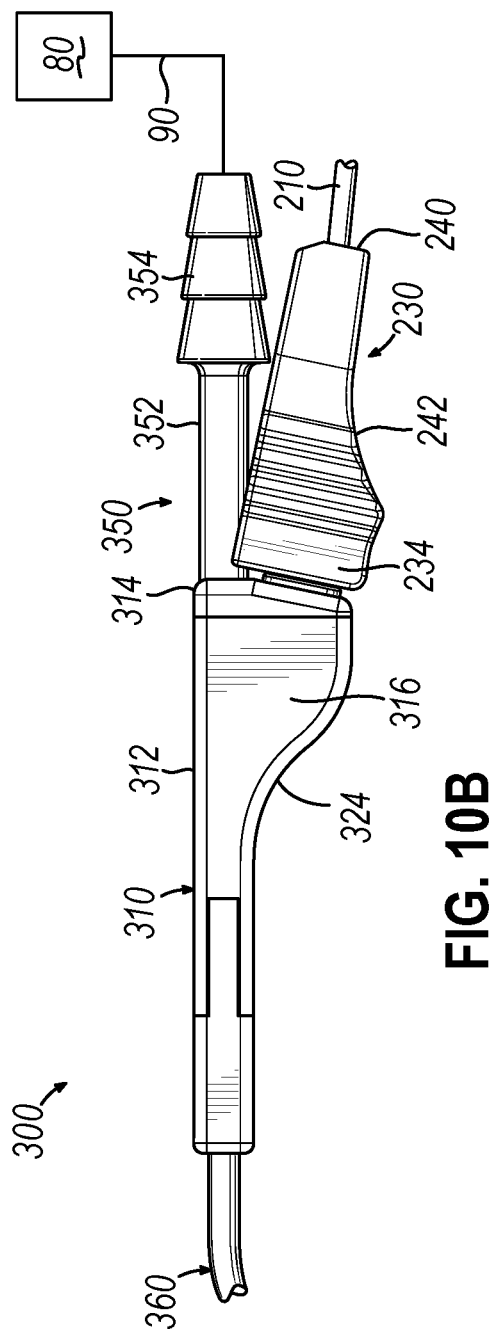
FIG. 10B depicts an assembled side elevational view of the distal coupling and the suction instrument of FIG. 9.

As shown in FIGS. 10A and 10B, planar proximal face (322) of grip portion (310) is angled downwardly relative to a vertical plane extending through grip portion body (312). Accordingly, distal coupling (230) is supported by grip portion (310) such that the longitudinal axis of distal coupling (230) is angled acutely relative to the longitudinal axis of grip portion (310) and suction conduit port (350). Such a configuration, in combination with the provision of recessed channel (250) of distal coupling (230), provides sufficient clearance for the distal end of suction conduit (90) fitted over suction conduit port (350). Additionally, distal coupling (230) in this angled configuration is suitably oriented such that the operator may rest his or her fingers against concavely contoured bottom surface (242) of distal coupling (230) as well as a concavely contoured bottom surface (324) of grip portion (310). This enables the operator's hand to assume a comfortable position about grip portion (310) and distal coupling (230) that minimizes strain on the operator's hand and wrist while still enabling the operator to effectively manipulate suction instrument (300).

In some versions, a distal portion of recessed channel (250) snugly abut proximal shaft portion (352) of suction conduit port (350), or the proximal end of suction conduit (90) fitted over port (350). As a result, distal coupling (230) is securely anchored relative to grip portion (310) such that electrical connectors (260, 330) are generally insulated from torque applied to distal coupling (230) (e.g., as a result of the operator's fingers exerting upwardly directed forces on bottom surface (242) of coupling (230)). Such torque might otherwise damage electrical connectors (260, 330) or cable assembly (200), and/or disrupt the electrical connection between connectors (260, 330).

Distal coupling (230) and/or grip portion (310) may include one or more seals (not shown) configured to provide a fluid-tight connection between electrical connector (330) and electrical connector (260) when distal coupling (230) is coupled with grip portion (310). For instance, and by way of example only, an o-ring seal may be provided on an outer surface of tubular member (264); on an inner wall of distal opening (252); or on an inner surface of connector socket (334). Alternatively, or in addition, annular rim (332) of grip portion connector (330) may comprise an elastomeric portion configured to sealingly engage the inner wall of distal opening (252) of distal coupling (230). Alternatively, or in addition, one or both of planar faces (238, 322) may include a gasket seal that encircles electrical connectors (260, 330) when distal coupling (230) and grip portion (310) are coupled together. Various other manners for providing a fluid-tight seal between distal coupling (230) and grip portion (310) will be readily apparent to those of ordinary skill in the art in view of the teachings herein.

B. Exemplary Alternative Distal Coupling of Shortened Length

As described above, distal coupling (230) of cable assembly (200) includes various features that enable distal coupling (230) to quickly and easily couple with grip portion (310) of suction instrument (300). In some instances, it may be desirable to minimize the length of distal coupling (230) to more easily accommodate suction conduit port (350) and suction conduit (90), and thereby reduce any risk of unwanted interference between distal coupling (230) and suction instrument (300).

Figure 11:
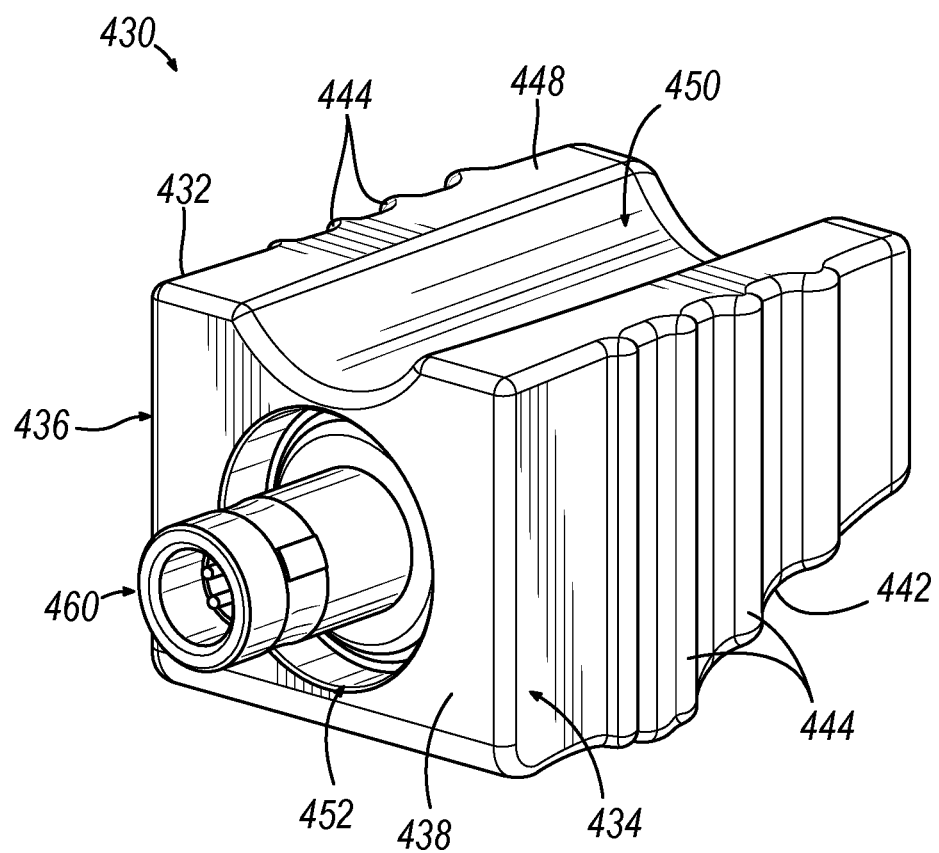
FIG. 11 depicts a distal end perspective view of an exemplary alternative distal coupling suitable for use with the cable assembly of FIG. 6.
Figure 12:
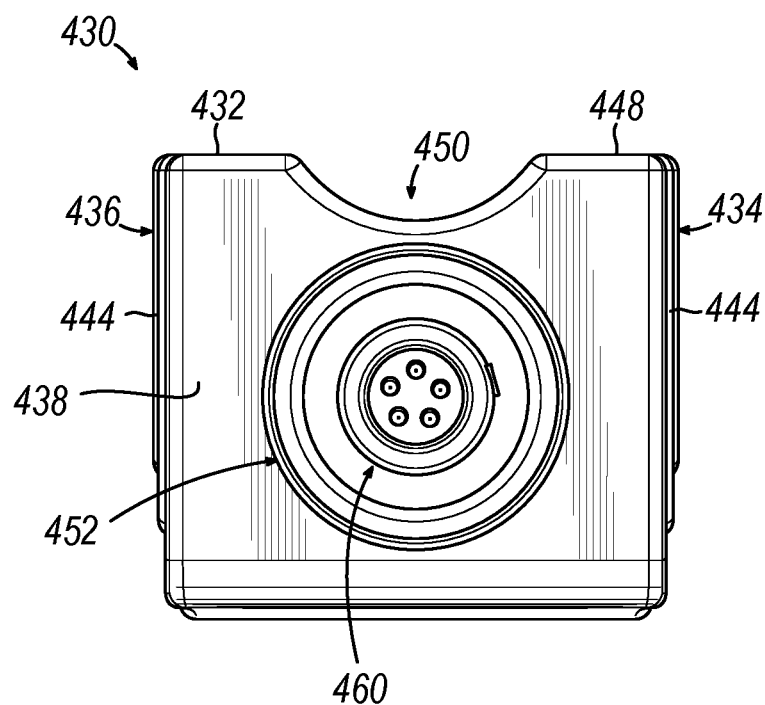
FIG. 12 depicts a distal end elevational view of the distal coupling of FIG. 11.
Figure 13:
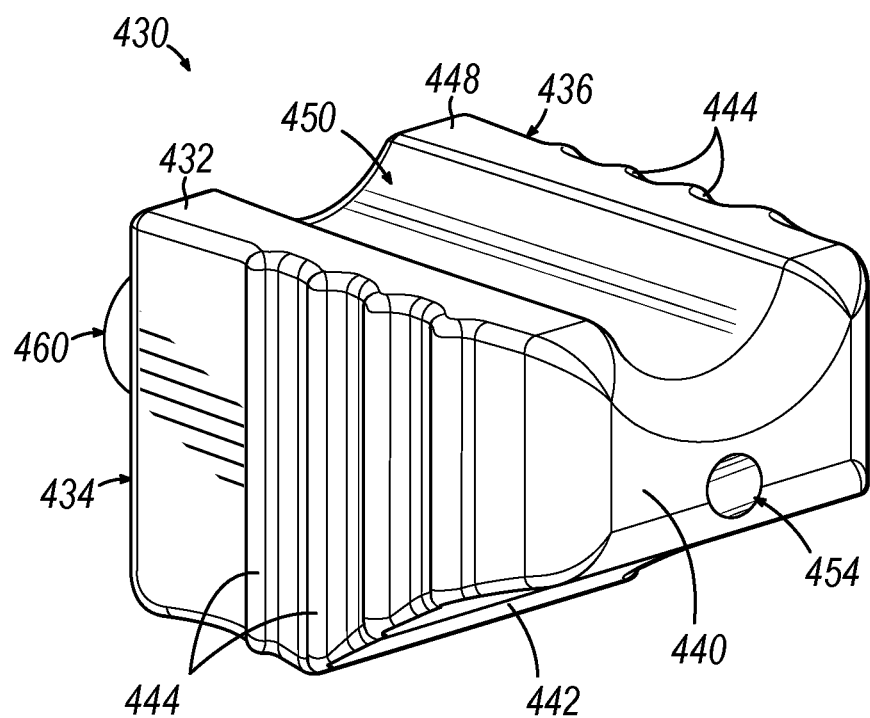
FIG. 13 depicts a proximal end perspective view of the distal coupling of FIG. 11.

FIGS. 11-13 show an exemplary alternative distal coupling (430) configured for use with cable assembly (200) in place of distal coupling (230) described above. Distal coupling (430) is similar to distal coupling (230) except that distal coupling (430) is truncated at its proximal end, as described below. Like distal coupling (230), distal coupling (430) includes a coupling body (432) having a first lateral side (434), an opposed second lateral (436), a planar distal face (438), and a concavely contoured bottom surface (442). Coupling body (432) further includes a plurality of ridges (444) disposed on each of the first and second lateral sides (434, 436).

As described above, distal coupling (230) terminates proximally with a rounded proximal end (240) that is spaced proximally from ridges (244) by concave depressions (446) so as to provide coupling body (232) with an elongate profile. In contrast, as shown best in FIG. 13, distal coupling (430) terminates proximally with a planar proximal face (440) disposed at a proximal end of ridges (444) so as to provide coupling body (432) with a truncated profile. Accordingly, distal coupling (430) is configured shorter in length than distal coupling (230) while maintaining the same distal end features that enable distal coupling (430) to couple with grip portion (310) of suction instrument (300).

Coupling body (432) further includes a top surface (448) and a recessed channel (450) formed therein that opens to planar distal face (438) at a distal end and to planar proximal face (440) at a proximal end. A distal opening (452) is formed in planar distal face (438) of coupling body (432), through which a portion of an electrical connector (460) housed within an interior of coupling body (432) projects. A proximal opening (454) is formed in planar proximal face (440) of coupling body (432), through which a proximal end of cable (210) is configured to extend to couple with electrical connector (460). Electrical connector (460) is similar in structure and function to electrical connector (260) described above, and is similarly configured to electrically couple with electrical connector (330) of suction instrument (300) when distal coupling (430) is coupled with grip portion (310).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument assembly, comprising: (a) a surgical instrument, wherein the surgical instrument comprises: (i) an instrument body, (ii) an elongate member extending distally from the instrument body, wherein a distal end of the elongate member is configured to be inserted into an anatomical passageway of a patient, (iii) a sensor operable to generate a signal corresponding to a location of the elongate member relative to anatomy of the patient, and (iv) a first electrical connector supported by the instrument body, wherein the first electrical connector is electrically coupled with the sensor; and (b) a cable assembly configured to couple with the surgical instrument, wherein the cable assembly comprises: (i) a cable, wherein a proximal end of the cable is configured to communicate with a processor, and (ii) a coupling disposed at a distal end of the cable, wherein the coupling is configured to releasably couple with the instrument body, wherein the coupling comprises: (A) a coupling body having a first lateral side and an opposed second lateral side that extend parallel to one another, wherein the first and second lateral sides are configured to extend parallel to at least one side of the instrument body when the coupling is coupled with the instrument body, and (B) a second electrical connector supported by the coupling body, wherein the second electrical connector is configured to electrically couple with the first electrical connector, wherein the cable assembly is configured to transmit the signal from the sensor proximally through the cable and toward the processor.

Example 2

The surgical instrument assembly of Example 1, wherein the instrument body includes a planar proximal face through which the first electrical connector is exposed, wherein the coupling body includes a planar distal face through which the second electrical connector is exposed, wherein the planar proximal and distal faces are configured to confront one another when the first and second electrical connectors are coupled together.

Example 3

The surgical instrument assembly of any of the preceding Examples, wherein the instrument body has a first lateral side and an opposed second lateral side that extend parallel to one another, wherein the first and second lateral sides of the coupling body are configured to extend parallel to the first and second lateral sides of the instrument body when the coupling is coupled with the instrument body.

Example 4

The surgical instrument assembly of any of the preceding Examples, wherein the first lateral side of the coupling body has a first gripping feature, wherein the second lateral side of the coupling body has a second gripping feature, wherein the first and second gripping features are configured to facilitate gripping of the coupling body by a user.

Example 5

The surgical instrument assembly of any of the preceding Examples, wherein the coupling body tapers proximally so as to define a concavely contoured bottom surface.

Example 6

The surgical instrument assembly of any of the preceding Examples, wherein the coupling body extends longitudinally along a coupling axis, wherein at least a portion of the coupling body has a rectangular cross-section transverse to the coupling axis.

Example 7

The surgical instrument assembly of Example 6, wherein the instrument body extends longitudinally along an instrument axis, wherein the coupling axis is configured to define an acute angle with the instrument axis when the coupling is coupled with the instrument body.

Example 8

The surgical instrument assembly of any of the preceding Examples, wherein the first electrical connector comprises a socket that houses a first electrical contact, wherein the second electrical connector comprises a tubular projection that houses a second electrical contact, wherein the socket is configured to receive the tubular projection to electrically couple the first and second electrical contacts together.

Example 9

The surgical instrument assembly of Example 8, wherein the tubular projection includes a key, wherein the socket includes a keyway configured to slidably receive the key when the first and second lateral sides of the coupling body are aligned parallel with the at least one side of the instrument body.

Example 10

The surgical instrument assembly of any of the preceding Examples, wherein the surgical instrument further comprises a first latch feature, wherein the coupling further comprises a second latch feature configured to lockingly engage the first latch feature when the coupling is coupled with the instrument body.

Example 11

The surgical instrument assembly of any of the preceding Examples, wherein the cable assembly further comprises a second coupling disposed at a proximal end of the cable, wherein the second coupling is configured to releasably couple with a component in electrical communication with the processor.

Example 12

The surgical instrument assembly of any of the preceding Examples, wherein the surgical instrument further comprises: (i) a suction lumen, and (ii) a suction port projecting from the instrument body and arranged in fluid communication with suction lumen, wherein the suction port is configured to communicate suction to the suction lumen from a suction source.

Example 13

The surgical instrument assembly of Example 12, wherein the coupling body further comprises a recessed channel configured to receive at least a portion of the suction port therein when the coupling is coupled with the instrument body.

Example 14

The surgical instrument assembly of any of Examples 12 through 13, wherein the suction port extends longitudinally along a first axis, wherein the coupling is configured to extend longitudinally along a second axis acutely angled to the first axis when the coupling is coupled with the instrument body.

Example 15

The surgical instrument assembly of any of Examples 12 through 14, wherein the suction lumen extends through the elongate member, wherein the sensor is arranged at a distal end of the elongate member.

Example 16

A cable assembly for use with a surgical instrument, the cable assembly comprising: (a) a cable, wherein a proximal end of the cable is configured to communicate with a processor; and (b) a coupling disposed at a distal end of the cable, wherein the coupling is configured to releasably couple with a surgical instrument, wherein the coupling comprises: (i) a coupling body extending longitudinally along a coupling axis, wherein the coupling body comprises: (A) a first lateral side having a first gripping feature, (B) a second lateral side parallel to the first lateral side, wherein the second lateral side has a second gripping feature, wherein the first and second gripping features are configured to facilitate gripping of the coupling body by a user, and (C) a top surface having a recessed channel, wherein the recessed channel extends parallel to the coupling axis and opens to a distal end of the coupling body, and (ii) an electrical connector supported by the coupling body, wherein the electrical connector is configured to releasably couple with an electrical connector of the surgical instrument to place the surgical instrument in electrical communication with the processor.

Example 17

The surgical instrument assembly of Example 16, wherein the coupling body tapers proximally so as to define a concavely contoured bottom surface extending between the first and second lateral sides.

Example 18

A method of communicating an electrical signal generated by a surgical instrument to an external processor via a cable assembly, wherein the cable assembly comprises a cable and a distal coupling configured to releasably couple with the surgical instrument, the method comprising: (a) receiving a distal end of the distal coupling with a proximal end of the surgical instrument, such that: (i) a lateral side of the distal coupling is oriented parallel to a lateral side of the surgical instrument, (ii) an electrical connector of the distal coupling electrically couples with an electrical connector of the surgical instrument, and (iii) a latch feature of the distal coupling engages a latch feature of the surgical instrument to releasably lock the distal coupling with the surgical instrument; (b) generating an electrical signal with a sensor of the surgical instrument; and (c) transmitting the electrical signal proximally through the electrical connectors and through the cable along an electrical path that communicates with the external processor.

Example 19

The method of Example 18, wherein the surgical instrument comprises a suction lumen and an outwardly projecting suction port in fluid communication with the suction lumen, wherein the distal coupling comprises a channel, wherein the method further comprises receiving at least a portion of the suction port into the channel while receiving the distal coupling with the surgical instrument.

Example 20

The method of Example 19, wherein the suction port extends along a first axis, wherein receiving the distal coupling with the surgical instrument further comprises supporting the distal coupling along a second axis that is acutely angled relative to the first axis.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. In some instances, the instrument may be placed in a reprocessing tray (e.g., a metal bin or basket) and then cleaned in a surgical instrument washer. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, steam, hydrogen peroxide vapor (e.g., via a STERRAD sterilization system by Advanced Sterilization Products of Irvine, Calif.), and/or using any other suitable systems or techniques.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument assembly, comprising:
   (a) a surgical instrument, wherein the surgical instrument comprises:
      (i) an instrument body,
      (ii) an elongate member extending distally from the instrument body, wherein a distal end of the elongate member is configured to be inserted into an anatomical passageway of a patient,
      (iii) a sensor operable to generate a signal corresponding to a location of the elongate member relative to anatomy of the patient,
      (iv) a first electrical connector supported by the instrument body, wherein the first electrical connector is electrically coupled with the sensor, and
      (v) a first latch feature; and
   (b) a cable assembly configured to couple with the surgical instrument, wherein the cable assembly comprises:
      (i) a cable, wherein a proximal end of the cable is configured to communicate with a processor, and
      (ii) a coupling disposed at a distal end of the cable, wherein the coupling is configured to releasably couple with the instrument body, wherein the coupling comprises:
         (A) a coupling body having a first lateral side and an opposed second lateral side that extend parallel to one another, wherein the first and second lateral sides are configured to extend parallel to at least one side of the instrument body when the coupling is coupled with the instrument body,
         (B) a second electrical connector supported by the coupling body, wherein the second electrical connector is configured to electrically couple with the first electrical connector, and
         (C) a second latch feature configured to lockingly engage the first latch feature when the coupling is coupled with the instrument body,
         wherein the cable assembly is configured to transmit the signal from the sensor proximally through the cable and toward the processor.

2. The surgical instrument assembly of claim 1, wherein the instrument body includes a planar proximal face through which the first electrical connector is exposed, wherein the coupling body includes a planar distal face through which the second electrical connector is exposed, wherein the planar proximal and distal faces are configured to confront one another when the first and second electrical connectors are coupled together.

3. The surgical instrument assembly of claim 1, wherein the instrument body has a first lateral side and an opposed second lateral side that extend parallel to one another, wherein the first and second lateral sides of the coupling body are configured to extend parallel to the first and second lateral sides of the instrument body when the coupling is coupled with the instrument body.

4. The surgical instrument assembly of claim 1, wherein the first lateral side of the coupling body has a first gripping feature, wherein the second lateral side of the coupling body has a second gripping feature, wherein the first and second gripping features are configured to facilitate gripping of the coupling body by a user.

5. The surgical instrument assembly of claim 1, wherein the coupling body tapers proximally so as to define a concavely contoured bottom surface.

6. The surgical instrument assembly of claim 1, wherein the coupling body extends longitudinally along a coupling axis, wherein at least a portion of the coupling body has a rectangular cross-section transverse to the coupling axis.

7. The surgical instrument assembly of claim 6, wherein the instrument body extends longitudinally along an instrument axis, wherein the coupling axis is configured to define an acute angle with the instrument axis when the coupling is coupled with the instrument body.

8. The surgical instrument assembly of claim 1, wherein the first electrical connector comprises a socket that houses a first electrical contact, wherein the second electrical connector comprises a tubular projection that houses a second electrical contact, wherein the socket is configured to receive the tubular projection to electrically couple the first and second electrical contacts together.

9. The surgical instrument assembly of claim 8, wherein the tubular projection includes a key, wherein the socket includes a keyway configured to slidably receive the key when the first and second lateral sides of the coupling body are aligned parallel with the at least one side of the instrument body.

10. The surgical instrument assembly of claim 1, wherein the cable assembly further comprises a second coupling disposed at a proximal end of the cable, wherein the second coupling is configured to releasably couple with a component in electrical communication with the processor.

11. The surgical instrument assembly of claim 1, wherein the surgical instrument further comprises:
    (i) a suction lumen, and
    (ii) a suction port projecting from the instrument body and arranged in fluid communication with suction lumen, wherein the suction port is configured to communicate suction to the suction lumen from a suction source.

12. The surgical instrument assembly of claim 11, wherein the coupling body further comprises a recessed channel configured to receive at least a portion of the suction port therein when the coupling is coupled with the instrument body.

13. The surgical instrument assembly of claim 11, wherein the suction port extends longitudinally along a first axis, wherein the coupling is configured to extend longitudinally along a second axis acutely angled to the first axis when the coupling is coupled with the instrument body.

14. The surgical instrument assembly of claim 11, wherein the suction lumen extends through the elongate member, wherein the sensor is arranged at a distal end of the elongate member.

15. The surgical instrument assembly of claim 1, wherein the coupling body further comprises a rounded end on a proximal end.

16. A cable assembly for use with a surgical instrument, the cable assembly comprising:
  (a) a cable, wherein a proximal end of the cable is configured to communicate with a processor; and
  (b) a coupling disposed at a distal end of the cable, wherein the coupling is configured to releasably couple with a surgical instrument, wherein the coupling comprises:
    (i) a coupling body extending longitudinally along a coupling axis,
      wherein the coupling body comprises:
        (A) a first lateral side having a first gripping feature,
        (B) a second lateral side parallel to the first lateral side, wherein the second lateral side has a second gripping feature, wherein the first and second gripping features are configured to facilitate gripping of the coupling body by a user, and
        (C) a top surface having a recessed channel, wherein the recessed channel extends parallel to the coupling axis and opens to a distal end of the coupling body, and
    (ii) an electrical connector supported by the coupling body, wherein the electrical connector is configured to releasably couple with an electrical connector of the surgical instrument to place the surgical instrument in electrical communication with the processor.

17. The cable assembly of claim 16, wherein the coupling body tapers proximally so as to define a concavely contoured bottom surface extending between the first and second lateral sides.

18. A method of communicating an electrical signal generated by a surgical instrument to an external processor via a cable assembly, wherein the cable assembly comprises a cable and a distal coupling configured to releasably couple with the surgical instrument, the method comprising:
  (a) receiving a distal end of the distal coupling with a proximal end of the surgical instrument, such that:
    (i) a lateral side of the distal coupling is oriented parallel to a lateral side of the surgical instrument,
    (ii) an electrical connector of the distal coupling electrically couples with an electrical connector of the surgical instrument, and
    (iii) a latch feature of the distal coupling engages a latch feature of the surgical instrument to releasably lock the distal coupling with the surgical instrument;
  (b) generating an electrical signal with a sensor of the surgical instrument; and
  (c) transmitting the electrical signal proximally through the electrical connectors and through the cable along an electrical path that communicates with the external processor.

19. The method of claim 18, wherein the surgical instrument comprises a suction lumen and an outwardly projecting suction port in fluid communication with the suction lumen, wherein the distal coupling comprises a channel, wherein the method further comprises receiving at least a portion of the suction port into the channel while receiving the distal coupling with the surgical instrument.

20. The method of claim 19, wherein the suction port extends along a first axis, wherein receiving the distal coupling with the surgical instrument further comprises supporting the distal coupling along a second axis that is acutely angled relative to the first axis.

* * * * *